US010093726B2

(12) United States Patent
Asmus et al.

(10) Patent No.: US 10,093,726 B2
(45) Date of Patent: Oct. 9, 2018

(54) PROTEIN SUSTAINED-RELEASE INJECTABLE FORMULATION

(71) Applicant: ESBATech—a Novartis Company LLC, Schlieren (CH)

(72) Inventors: Lutz Asmus, Geneva (CH); Michael Möller, St-Cergue (CH); Robert Gurny, Geneva (CH); John P. A. Grimshaw, Zurich (CH)

(73) Assignee: ESBATech, an Alcon Biomedical Research Unit LLC, Schlieren (CH)

( * ) Notice: Subject to any disclaimer, the term of this patent is extended or adjusted under 35 U.S.C. 154(b) by 0 days.

(21) Appl. No.: 15/245,767

(22) Filed: Aug. 24, 2016

(65) Prior Publication Data

US 2016/0362483 A1 Dec. 15, 2016

Related U.S. Application Data

(62) Division of application No. 14/462,065, filed on Aug. 18, 2014, now Pat. No. 9,873,736, which is a division of application No. 13/756,932, filed on Feb. 1, 2013, now abandoned.

(60) Provisional application No. 61/594,099, filed on Feb. 2, 2012.

(51) Int. Cl.
| | |
|---|---|
| *C07K 16/22* | (2006.01) |
| *A61K 9/10* | (2006.01) |
| *A61K 47/34* | (2017.01) |
| *A61K 9/00* | (2006.01) |
| *A61K 39/395* | (2006.01) |
| *C08J 3/12* | (2006.01) |
| *A61K 9/16* | (2006.01) |
| *A61K 39/00* | (2006.01) |

(52) U.S. Cl.
CPC ............ *C07K 16/22* (2013.01); *A61K 9/0048* (2013.01); *A61K 9/0051* (2013.01); *A61K 9/10* (2013.01); *A61K 9/1647* (2013.01); *A61K 39/3955* (2013.01); *A61K 39/39591* (2013.01); *A61K 47/34* (2013.01); *C08J 3/12* (2013.01); *A61K 2039/505* (2013.01); *C07K 2317/24* (2013.01); *C07K 2317/622* (2013.01); *C07K 2317/94* (2013.01)

(58) Field of Classification Search
CPC ................ C07K 16/22; C07K 2317/24; C07K 2317/622; C07K 2317/94; A61K 9/10; A61K 9/1467; A61K 47/34
See application file for complete search history.

(56) References Cited

U.S. PATENT DOCUMENTS

| | | |
|---|---|---|
| 2009/0117171 A1 | 5/2009 | Francois et al. |
| 2009/0281068 A1 | 11/2009 | Moller et al. |
| 2013/0202605 A1 | 8/2013 | Asmus |

FOREIGN PATENT DOCUMENTS

| | | |
|---|---|---|
| AU | 775778 B2 | 8/2004 |
| WO | 200040262 A1 | 7/2000 |
| WO | 2009155724 A2 | 12/2009 |
| WO | 2011015634 A2 | 2/2011 |
| WO | 2012051734 A1 | 4/2012 |

OTHER PUBLICATIONS

Asmus et al., Eur. J Pharmaceuticals and Biopharmaceutics 95: 250-260, 2015.*
Asmus et al.; "Solutions as solutions—synthesis and use of a liquid polyester excipient to dissolve lipophilic drugs and formulate sustained-release parenterals"; European Journal of Pharmaceutics and Biopharmaceutics; vol. 79; pp. 584-591 (2011).
Bourges et al.; "Intraocular implants for extended drug delivery: Therapeutic applications"; Advanced Drug Delivery Reviews; vol. 68; pp. 1182-1202 (2006).
Boyer and Posalski; "Potential complication associated with removal of ganciclovir implants"; Brief Reports: American Journal of Ophthalmology; vol. 127; No. 3; pp. 349-350 (Mar. 1999).
Einmahl et al.; "A viscous bioerodible poly(ortho ester) as a new biomaterial for intraocular application"; J. Biomed Mater Res.; vol. 50; pp. 566-573 (2000).
Sintzel et al.; Synthesis and characterization of self-catalyzed poly(ortho ester); Biomaterials; vol. 19; pp. 791-800 (1998).
Jaffe et al.; "Long-term follow-up results of a pilot trial of a fluocinolone acetonide implant to treat posterior uveitis"; Ophthalmology; vol. 112; pp. 1192-1198 (2005).
Kimura and Ogura; "Biodegradable polymers for ocular drug delivery"; Ophthalmologica; vol. 215; pp. 143-155 (2001).
Kupperman et al.; "Randomized controlled study of an intravitreous dexamethasone drug delivery system in patients with persistent macular edema"; Clinical Trials; Arch Ophthalmol.; vol. 125; pp. 309-317 (2007).
Hassan et al.; "Composite microparticles with in vivo reduction of the burst release effect"; European Journal of Pharmaceutics and Biopharmaceutics; vol. 73; pp. 337-344 (2009).
Miller and Appen; Walsh and Hoyt's clinical neuro-ophthalmology; Arch Ophthalmol; vol. 115; p. 138 (Jan. 1997).
Musch et al.; "Treatment of cytomegalovirus retinitis with a sustained-release ganciclovir implant"; New England Journal of Medicine; vol. 337; No. 2; pp. 83-90 (1997).
Sintzel et al.; Influence of irradiation sterilization on a semi-solid poly(ortho ester); International Journal of Pharmaceutics; vol. 175; pp. 165-176 (1998).
Trimaille et al.; "Synthesis and ring-opening polymerization of new monoalkyl-substituted lactides"; Journal Polym Sci.; Part A: Polym Chem; vol. 42; pp. 4379-4391 (2004).

(Continued)

*Primary Examiner* — Phuong Huynh
(74) *Attorney, Agent, or Firm* — Jason J. Derry (57) ABSTRACT

The present invention provides sustained-release pharmaceutical formulations for administering proteins to the eye. In particular, the invention provides formulations comprising single chain antibodies and hydrophobic polyester hexylsubstituted poly(lactic acid) (hexPLA). The invention further provides processes for the production of sustained-release pharmaceutical formulations and medical uses thereof.

1 Claim, 9 Drawing Sheets

Specification includes a Sequence Listing.

(56) References Cited

OTHER PUBLICATIONS

Stancovski, et al: "Mechanistic aspects of the opposing effects of monoclonal antibodies to the ERBB2 receptor on tumor growth", PNAS 88:8691-8695, 1991.
Golay et al: "Mechanism of action of therapeutic monoclonal antibodies: promises and pitfalls of in vitro and in vivo assays", Archives of Biochemistry and Biophysics 526: 146-153, 2012.
Yu et al: Investigative Ophthalmology & Visual Science 49(2): 522-527, Feb. 2008.

* cited by examiner

PROTEIN SUSTAINED-RELEASE INJECTABLE FORMULATION

FIELD OF THE INVENTION

The present invention relates to sustained-release pharmaceutical formulations for administering proteins to the eye. In particular, the invention relates to formulations comprising single chain antibodies and hydrophobic polyester hexylsubstituted poly(lactic acid) (hexPLA). The invention further relates to processes for the production of sustained-release pharmaceutical formulations and medical uses thereof.

BACKGROUND OF THE INVENTION

A number of intravitreal sustained-release pharmaceuticals for small molecules have been investigated and marketed in the past years. Early implants delivering Ganciclovir (Vitrasert®) and Fluocinolone (Retisert®) showed long release periods but were non-biodegradable (Musch et al., 1997, *New England Journal of Medicine* 337:83; Jaffe et al., 2005, *Ophthalmology* 112:119). A number of adverse effects, material problems, and surgical problems were reported when removing the implants from the eye (Martin et al., 1997, *Arch Ophthalmol-Chic* 115:1389; Boyer et al., 1999, *Am J Ophthalmol* 127:349). Thus, interest shifted toward biodegradable implants.

The currently approved degradable implants for intravitreal application (Ozurdex®) are based on poly(lactic-co-glycolic acid) (PLGA) and release dexamethasone for around 6 months (Kuppermann et al., 2007, *Arch Ophthalmol-Chic* 2007, 125:309). For the preparation of the PLGA-implants, pressure, heat, solvents or a combination thereof is used to incorporate the active substance and to form the implant (Kimura et al., 2001, *Ophthalmologica* 215:143). This implies problems for the formulation of proteins due to their intrinsically lower stability as compared to many small molecules.

A possible solution to the formulation problem of proteins for sustained-release could be the use of viscous excipients instead of solid implants. These can simply be mixed with the lyophilized protein to form the final formulation. Poly(ortho esters) (POEs) of the third generation were the first viscous, polymeric liquids investigated toward sustained intravitreal release (Einmahl et al., 2000, *J Biomed Mater Res* 50:566). But due to the lack of storage stability (Merkli et al., 1996, *Biomaterials* 17:897), difficulties with sterilizability (Sintzel et al., 1998, *International Journal of Pharmaceutics* 175:165) and difficulties in synthesis and upscaling (Behar-Cohen et al., 2006, *Advanced Drug Delivery Reviews* 58:1182), they were soon followed by a new generation of POEs.

Fourth generation POEs (POEs IV) were easier to synthesize, and a control of the degradation rate was possible by adjusting the ratio of the used monomers (Gurny et al., 1998, *Biomaterials* 19:791). POEs IV were evaluated up to a clinical phase II study and showed good biocompatibility in the human eye (Behar-Cohen et al., 2006, *Advanced Drug Delivery Reviews* 58:1182). However, their period of degradation in vivo was much longer than the period of drug release, shifting interest toward new liquid polymer entities for sustained-release delivery in the eye. Consequently, there is a need for improved sustained-release delivery systems and formulations for administering proteins to treat ocular diseases.

SUMMARY OF THE INVENTION

The invention provides sustained-release pharmaceutical formulations, comprising a single chain antibody Fv fragment (scFv) and hydrophobic polyester hexylsubstituted poly(lactic acid) (hexPLA). In one aspect, a formulation of the invention is for ocular administration to a subject in need thereof.

In certain aspects, a formulation of the invention comprises a scFv present in a final molecular weight of at least about 1.25% (w/w).

In other aspects, a formulation of the invention comprises hexPLA present at a concentration of at least about 1500 g/mol.

In one aspect, an intravitreal sustained-release depot comprising the formulation of the invention is provided.

In another aspect, the invention provides a delivery system comprising the sustained-release pharmaceutical formulation of a scFv and hexPLA and a syringe.

The invention further provides a process for the preparation of a sustained-release pharmaceutical formulation, the process comprising cryo-milling a scFv and hydrophobic polyester hexylsubstituted poly(lactic acid) (hexPLA). In certain aspects, the process further comprises warming the formulation to room temperature under vacuum.

The invention also provides methods of treating an ocular disorder in a patient, comprising administering to the patient an effective amount of the sustained-release pharmaceutical formulation of a scFv and hexPLA.

In addition, the invention provides a stable single chain antibody formulation, comprising a single chain antibody and hexylsubstituted poly(lactic acid) (hexPLA), wherein the single chain antibody is stable at 37° C.

Specific preferred embodiments of the invention will become evident from the following more detailed description of certain preferred embodiments and the claims.

multiple administration systems. In certain embodiments, a formulation of the invention is administered by ocular tissue injection such as periocular, conjunctival, subtenon, intracameral, intravitreal, intraocular, subretinal, subconjunctival, retrobulbar, or intracanalicular injections. In a preferred embodiment, the formulation is administered to the patient by intravitreal administration. For example, for such purposes, the formulation may be injected using a syringe. Accordingly, in one aspect the present invention also provides a delivery system which contains the liquid formulation selected from the group of single use injection syringes.

In certain embodiments, a delivery system comprises a container. Suitable containers include, for example, bottles, vials (e.g. dual chamber vials), syringes (such as dual chamber syringes) and test tubes. The container may be formed from a variety of materials such as glass or plastic. The container holds the formulation and the label on, or associated with, the container may indicate directions for use. The label may for example indicate that the formulation is useful or intended for intravitreal administration. The container holding the formulation may be a multi-use vial, which allows for repeat administrations (e.g. 2-6 administrations) of the formulation.

Accordingly, also provided is the use of the formulation according to the invention for the production of a delivery system for use in the treatment of a disease.

In another embodiment of the invention, an article of manufacture is provided which contains the formulation of the present invention and provides instructions for its use. Thus, an article of manufacture is provided herein which comprises: a) container which holds a concentrated formulation of a single chain antibody and hexPLA; and b) instructions for use.

The article of manufacture may further include other materials desirable from a commercial and user standpoint, including other buffers, diluents, filters, needles, syringes, and package inserts with instructions for use.

IV. Processes for Preparation

The invention also provides a process for preparing a sustained-release formulation comprising a single chain antibody and hexPLA.

The poly(lactic acid) (PLA) derivative hexylsubstituted poly(lactic acid) (hexPLA; poly(2-hydroxyoctanoic acid)), wherein all methyl groups along the PLA-backbone are substituted by hexyl groups, is a viscous liquid at room-temperature. It can be synthesized by ring-opening polymerization (Trimaille et al., 2004, *Journal of Polymer Science Part A-Polymer Chemistry* 42:4379) as well as by a green-chemistry polycondensation (Asmus et al., 2011, *European Journal of Pharmaceutics and Biopharmaceutics* 79:584). Preparation of hexPLA is described in the Examples herein. HexPLA is stable under dry heat sterilization conditions and formulations with small, lipophilic molecules released the active compound over several weeks.

Prior to formulation, the single chain antibody for formulation is preferably lyophilized as described herein. Lyophilization can be accomplished using well-known techniques in the art.

In certain embodiments, a formulation of the invention is prepared by cryo-milling. For example, lyophilized single chain antibody protein and the hexPLA polymer are slowly frozen to −80° C. and milled together in a SPEX 6700 Freezer/Mill (SPEX Industries, Edison, USA) under liquid nitrogen for 5 minutes. This cryo-milling procedure simultaneously reduces the particle size of the solid compound and homogeneously disperses it in the polymer matrix to form a suspension formulation. In certain embodiments, after milling, the formulation is slowly warmed to room-temperature under conditions suitable to avoid water condensation on the product (e.g., vacuum, inert gas, or hermetically closed cylinders). In other embodiments, mixing of a single chain antibody and hexPLA is carried out at a temperature at which the lyophilized single-chain protein is stable, preferably at temperatures below room-temperature, preferably at cooled conditions, preferably at temperatures below the glass transition point of the hexPLA polymer, preferably under cryo-milling.

Further provided is a process for preparing a sustained-release formulation comprising a single chain antibody and hexPLA for therapeutic applications, wherein: a single chain antibody is lyophilized, and the lyophilized antibody and hex-PLA are frozen and milled together to form a suspension.

In certain embodiments, the freezing step is carried out slowly to a temperature of −80° C., and the milling step is carried out under liquid nitrogen for about 5 minutes.

In another embodiment, the process further comprises warming the resulting suspension to room temperature or a slightly warmer temperature (e.g., 25° C.).

V. Medical Uses

The present invention also provides the formulation of the invention for use in medicine. In particular, the use of the formulation for the manufacture of a medicament for the treatment of disease, such as an ocular disease, is provided.

In certain embodiments, the ocular disease is a retinal disease, such as a disease associated with ocular neovascularization. In certain embodiments, the ocular disease is macular degeneration, diabetic retinopathy, sequela associated with retinal ischemia, and posterior segment neovascularization, retinal edema, geographic atrophy, diabetic macular edema, and the like.

The appropriate dosage of the antibody will depend, for example, on the condition to be treated, the severity and course of the condition, whether the protein is administered for preventive or therapeutic purposes, previous therapy, the patient's clinical history and response to the protein, the type of antibody used, and the discretion of the attending physician. The antibody is suitably administered to the patient at one time or over a series of treatments and may be administered to the patient at any time from diagnosis onwards. The antibody may be administered as the sole treatment or in conjunction with other drugs or therapies useful in treating the condition in question.

Depending on the disease or disorder to be treated, a therapeutically effective amount of the antibody may be administered to the patient.

The contents of any patents, patent applications, and references cited throughout this specification are hereby incorporated by reference in their entireties.

Unless otherwise required by context, singular terms used herein shall include pluralities and plural terms shall include the singular.

EXAMPLES

The present disclosure is further illustrated by the following examples, which should not be construed as further limiting. The contents of all Figures and all references, patents and published patent applications cited throughout this application are expressly incorporated herein by reference in their entireties.

Materials

The humanized antibody-fragment ESBA903 was produced and lyophilized in-house by ESBATech, an Alcon Biomedical Research Unit (Schlieren, Switzerland). Three mL ESBA903 (10 mg/ml in 20 mM Na-citrate, pH 6.25) were added to 10 mL tubular-type vials, covered with bromobutyl stoppers that are suitable for lyophilization. Lyophilization was performed using a VirTis AdVantage Plus freeze dryer (Wizard 2.0 process controller, SP Scientific, Warminster, USA), equipped with an intergrated stoppering mechanism and a Leybold Trivac B high-performance vacuum pump (D4B/D6B, Oerlikon Corporate, Switzerland). The process was controlled using the actual shelf-temperature, and process data were recorded (Mentor/Wizard Synoptic 6.0, SP Scientific, Warminster, USA). Product temperature was recorded using thermocouples that had been placed in lyophilization vials. Vials were frozen to −55° C.; after evacuation of the lyophilization chamber (0.15 mbar), the shelf temperature was ramped to −10° C. in the course of several hours. Secondary drying was performed at 25° C. under full vacuum. The freeze dryer was floated with nitrogen gas before stoppering to avoid re-introduction of humidity and to minimize potential oxidative degradation processes. After reconstitution the protein proved fully monomeric.

Hexylsubstituted poly(lactic acid) (hexPLA) was synthesized by polycondensation of 2-hydroxyoctanoic acid as published (Asmus et al., 2011, *European Journal of Pharmaceutics and Biopharmaceutics* 79:584). Briefly, the polymers of 2500 g/mol and 5000 g/mol were synthesized by heating the monomer to 120° C. using 0.5 mol % sulfuric acid (Acros Organics, New Jersey, USA) as polycondensation catalyst. The reactions were performed under an oil-pump vacuum of 0.001 bar until the appropriate molecular weight was obtained. The polymers were purified by precipitation from acetone into aqueous 0.1 M $NaHCO_3$, then dissolved in acetone, filtered over Celite® 545 coarse and the solvent removed under vacuum. The hexPLA polymers of 1500 g/mol and 3500 g/mol were prepared by an improved method, without the use of a catalyst. The monomer was simply heated to 150° C. and the melt was stirred under a vacuum of 0.001 bar. No additional synthesis steps or purifications were performed on these hexPLA polymers due to the absence of any additional substances like catalysts or solvents. All four polymers were sterilized using a standard European Pharmacopoeia dry heat sterilization method by heating them to 180° C. for 30 min. The molecular weight was determined by gel permeation chromatographie (GPC) using a Waters 515 HPLC pump, Waters 410 injector, Styragel HR 1-4 columns and Waters 717 GPC-detector (Waters Corporation, Milford, USA). The continuous phase was THF. Polystyrene standards (PSS, Mainz, Germany) were used for calibration. All chemicals and solvents were used as received.

Example 1

Formulation Preparation and Characterization

The lyophilized ESBA903 protein and the hexPLA polymer were slowly frozen to −80° C. and milled together in a SPEX 6700 Freezer/Mill (SPEX Industries, Edison, USA) under liquid nitrogen for 5 min. This cryo-milling procedure simultaneously reduced the particle size of the solid compound and homogeneously dispersed it in the polymer matrix to form a suspension formulation. After milling, the formulation was slowly warmed to room-temperature under vacuum to avoid water condensation on the product.

In total, seven formulations were prepared with drug loadings in the range between 1.25% and 5.0% (w/w) protein in polymer, with weight average molecular weights from 1500 g/mol to 5000 g/mol (Table 1). The particle size of the incorporated lyophilisate and the homogeneous distribution inside the hexPLA were verified by optical microscopy using an Optiphot-2 microscope (Nikon, Tokyo, Japan).

TABLE 1

| | | Polymer molecular weight $M_W$ | | | |
|---|---|---|---|---|---|
| | | 1500 g/mol | 2500 g/mol | 3500 g/mol | 5000 g/mol |
| Protein | 1.25% | — | ✓ | — | — |
| loading | 2.50% | ✓ | ✓ | ✓ | ✓ |
| [w/w] | 5.00% | — | ✓ | — | ✓ |

Lyophilized ESBA903 formed suspensions with the viscous, lipophilic polymer hexyl-substituted poly(lactic acid) (hexPLA). Accordingly, the particle size of the incorporated protein lyophilisate was a key factor for the suitability of ESBA903-hexPLA formulations as injectables for an ophthalmic application, as the solid lyophilisate particles need to be small enough and homogenously dispersed to allow good injectability through narrow needles, physical suspension stability and controlled release from the matrix. For proteins, the formulation process is critical because shear stress and warming of the active compound can alter the protein structure and thus its activity. Therefore, a preparation method limiting these influences is necessary. Cryo-milling of the ESBA903 lyophilisate together with the polymer matrix was the method of choice because it allowed simultaneous milling of the solid particles and distribution in the polymer. The liquid nitrogen prevented the formation of heat spots during the milling process, reducing the risk of protein denaturation.

FIG. 1 displays an optical microscopy image of a formulation obtained by the cryo-milling method (FIG. 1). The particle size was efficiently reduced during the process from up to 200 μm in diameter to less than 10 μm, with a majority of particles being smaller than 2 μm. The small particle size allowed injection of the suspension formulation through narrow needles with an inner diameter of about 210 μm, like 27 G hypodermic needles. This fast and simple single step micronization and formulation process was suitable to prepare suspension formulations of ESBA903 with hexPLA.

Example 2

Formulation Rheology and Injectability

Seven ESBA903-hexPLA formulations (Table 1) were prepared to investigate the influence of the drug loading and polymer molecular weight on the rheology and injectability characteristics. The rheological behavior of the protein formulations is important for the injectability and the suspension stability. Two inherent factors influencing the viscosity, the hexPLA molecular weight and the ratio of incorporated drug, were separately studied in dependence of the formulation temperature.

The rheological behavior of the formulations was investigated using a RheoStress 1 Haake stress rheometer (Vreden, Germany), a cone-plate set-up with 0.10 mm gap spacing, 2° angle and a plate diameter of 35 mm. The measurements were performed at a shear rate of 0.1 s$^{-1}$ and a heating cycle of 10 min ranging from 15° C. to 37° C.

Figure 1:
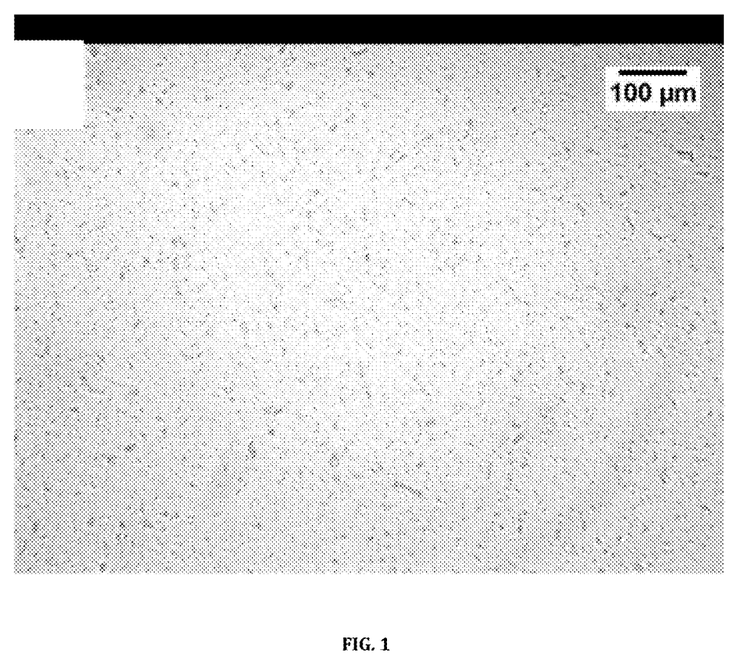
FIG. 1 shows optical microscopy images of a formulation containing 1.25% ESBA903 in hexPLA of 2500 g/mol formulated after cryo-milling.
Figure 2A:
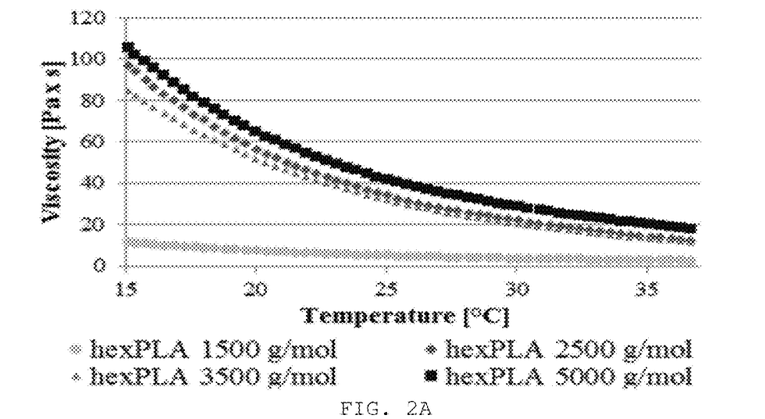
FIG. 2A shows change in viscosity of ESBA903-hexPLA formulations with increasing temperature and dependence of viscosity on polymer molecular weight at a constant drug loading of 2.5%.
Figure 2B:
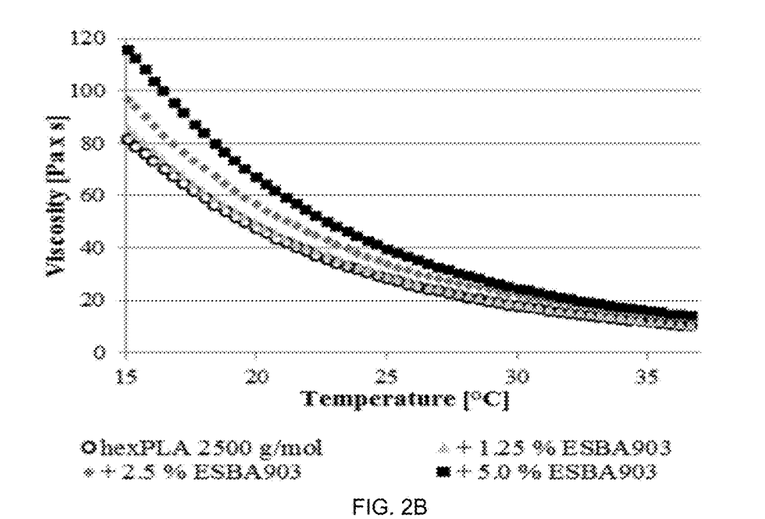
FIG. 2B shows change in viscosity of ESBA903-hexPLA formulations with increasing temperature and dependence of viscosity on drug loading at a constant molecular weight of 2500 g/mol.
Figure 3A:
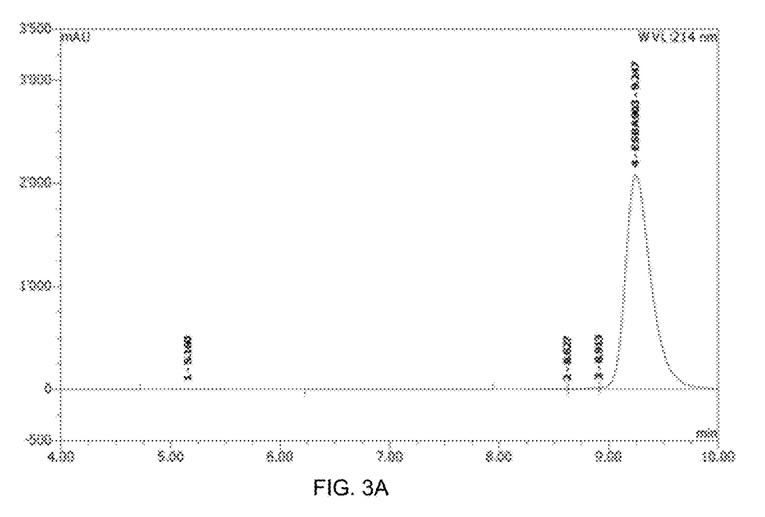
FIG. 3A shows a SEC-HPLC chromatogram of ESBA903 reference.
Figure 3B:
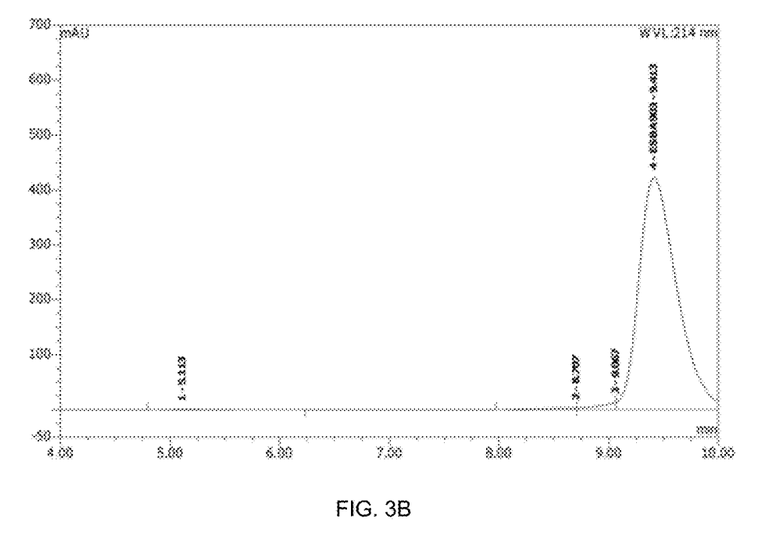
FIG. 3B shows a SEC-HPLC chromatogram of ESBA903 after extraction from a formulation with hexPLA that had been prepared by cryo-milling.
Figure 4:
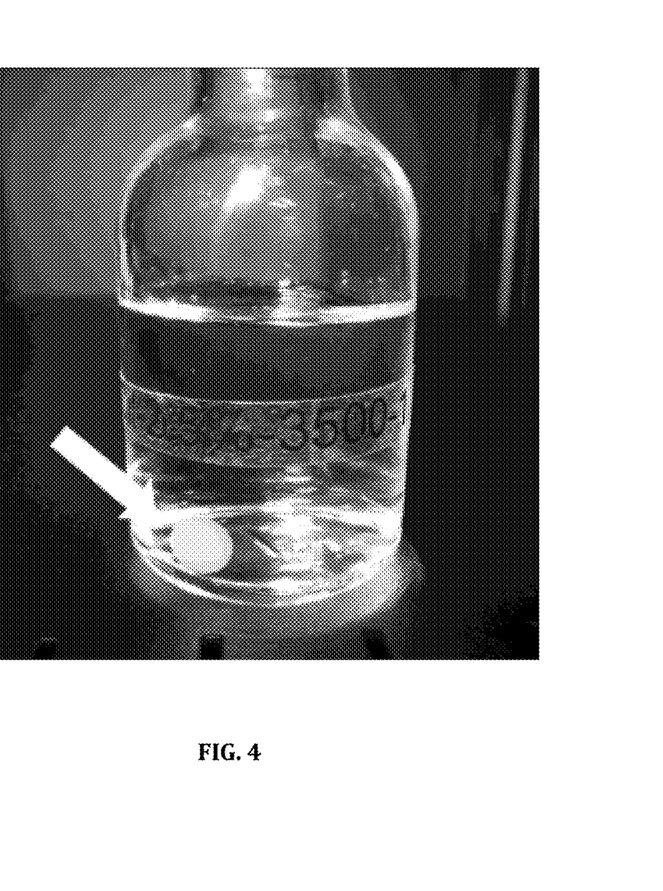
FIG. 4 shows ESBA903-hexPLA formulation in citrate buffer forming a spherical droplet depot.

FIGS. 2A and 2B show that the viscosity of all formulations was significantly influenced by the temperature, displaying lower viscosities at higher temperatures. This behavior was due to better flexibility of the polymer chains at higher temperatures resulting in less interaction between the macromolecules. The high viscosity at low temperatures may increase the storage stability of the suspension because sedimentation of the active compound may be reduced in highly viscous media, in addition to the effect of the small particle size, as expressed by the law of Stokes. Furthermore, warming to room- or body-temperature resulted in formulations, of which therapeutic doses were injectable even through thin 27 G-needles, typically applied in ophthalmic treatments.

However, the ease of injection was highly dependent on the polymer molecular weight, an important factor influencing the viscosity of the formulation, as can be seen in FIG. 2A. The increase from 1500 g/mol to 2500 g/mol resulted in a 5-fold augmentation of the viscosity. For molecular weights above 2500 g/mol the difference was less pronounced. The polymer of 3500 g/mol showed a slightly lower viscosity, due to its slightly higher polydispersity (PD). The 2500 g/mol polymer had a PD of 1.55 and the 3500 g/mol polymer a PD of 1.62 attributed to the simplified catalyst free synthesis method used for the latter polymer. Due to the direct use without purification more of the small polymer chains remained in the matrix. These small polymer chains or oligomers present in the hexPLA act as internal plasticizers since they are too small to get entangled and therefore decrease the viscosity.

As expected, higher drug loadings resulted in an increase in viscosity of the formulations because the incorporated particles hinder the free flow of the liquid hexPLA polymer. As displayed in FIG. 2B the addition of 5.0% ESBA903 lyophilisate to the polymer of 2500 g/mol resulted in a viscosity increase by 35% at 37° C. compared to the pure polymer. Thus, the protein-hexPLA formulations behaved like typical suspensions and the easiness of injection was influenced by the drug loading. However, a drug loading of 5.0% was possible regarding injectability.

In the investigated range between 15 and 37° C. the correlation between temperature and viscosity can be expressed by a simple exponential equation for all formulations with correlation coefficients higher than 0.99 in the form: $y=m\times e^{(n\times x)}$.

The exponential factor (n) is determined by the type of polymer and thus, by the molecular weight, while the multiplication factor (m) depends on the rate of drug loading. Therefore, the viscosity of an ESBA903-hexPLA formulation can be calculated for a certain drug loading and defined temperature if the pure polymer was previously characterized for its rheology.

Injectability of parenteral formulations was examined with the needle length set to 12 mm as generally used for intraocular injections and the inner diameter to 0.210 mm, corresponding to a 27 G needle. Depending on the drug loading, an amount of 50 μL of formulation should be sufficient for a treatment period of 3 to 6 months. To allow a fast and practical injection by the ophthalmologist, the application process should last less than 15 seconds. A 0.5 mL syringe suitable for the application of 50 μL of ESBA903-hexPLA has a typical inner plunger diameter of around 4.0 mm. Finally, the maximal applicable force for good injectability was fixed at 50 N. Using these parameters, viscosity below 38 Pa×s allows easy injection, according to the law of Hagen-Poiseuille. As displayed in FIG. 2, all investigated formulations with polymer molecular weights below 3500 g/mol were thus injectable at room-temperature or after slightly warming to 25° C., and no further excipients like solvents or plasticizers were needed for the application.

Example 3

ESBA903-hexPLA Compatibility

The influence of the formulation process on the protein conformation was analyzed by size exclusion chromatography (SEC), with which ESBA903 monomers could be separated from dimers and other oligomers and quantified. Therefore, the protein was extracted from two formulations containing 5.0% protein in hexPLA of 2500 g/mol and 5000 g/mol immediately after the cryo-milling preparation process, and the extracts were compared to the pure single chain antibody fragment of the original lyophilisate.

The humanized VEGF-antibody fragment ESBA903 was quantified and the monomer ratio of the protein was assessed using size exclusion chromatography (SEC). The analyses were performed on a Dionex Ultimate 3000 HPLC system (Sunnyvale, Calif., USA) equipped with a TSK-Gel Super SW2000, 4.6 mm×30 cm columns (Tosoh Bioscience, Yamaguchi, Japan). An isocratic method was used with a flow rate of 0.35 mL/min of PBS running buffer (25 mM $Na_2HPO_4$, 0.1 M NaCl, pH 6.5). The column temperature was maintained at 30° C., and the protein was detected by UV absorption at 214 nm. Calibration standard solutions of ESBA903 were prepared in citrate buffer (20 mM sodium citrate, 125 mM NaCl, pH-value 6.25), and the sample solutions were analyzed as such. The applied method allowed separation of ESBA903 monomers from lower-order oligomers and soluble aggregates.

10 mg of the two formulations containing 5.0% ESBA903 in hexPLA of 2500 g/mol and 5000 g/mol, respectively were dispersed in three Eppendorf cups each. 0.7 mL citrate buffer (20 mM sodium citrate, 125 mM NaCl, pH 6.25) was added and the protein was extracted for 1.5 hours. Three different extraction methods were used to eliminate an influence of the handling during the extraction process on the protein conformation: i) gentle agitation, ii) incubation at 37° C. and shaking at 60 rpm (in vitro release conditions), iii) intense vortexing. Afterwards, the supernatant samples were analyzed regarding the monomer to multimer ratio by SEC-HPLC.

As displayed in FIG. 3, SEC-HPLC revealed no significant difference in the SEC-chromatograms between the ESBA903 reference (FIG. 3A) and the extracted protein from the hexPLA formulations (FIG. 3B). The protein molecules were existent mainly as monomers with less than 3% of dimers and other oligomers present, independent of the extraction method. Since no oligomers were formed during the preparation process, while being incorporated in the lipophilic polymer or during extraction, hexPLA did not induce the formation of ESBA903 oligomers. This is presumably due to the incorporation of the protein into the matrix as a solid lyophilisate, in which the ESBA903 is stable, and interactions with the liquid excipient are limited to the lyophilisate surface. The cryo-milling process also showed suitability for the micronization and distribution of ESBA903 in the polymer matrix since the protein remained in its active monomer form after the process. Milling in liquid nitrogen efficiently prevented heating of the active substance and thermo-related degradation of the protein. Finally, ESBA903 was released from the hexPLA matrix into citrate buffer without apparently undergoing conformational modifications. These results proved the hexPLA suitability as an excipient for sustained-release formulations of ESBA903 due to its compatibility with the single chain antibody fragment. Also, cryo-milling is a feasible method to efficiently micronize the lyophilized protein preparation and simultaneously prepare homogeneous suspension formulations without altering the protein conformation.

Example 4

ESBA903 Storage Stability in hexPLA

The storage stability of ESBA903 in the hexPLA matrix was assessed with suspension formulations containing 5.0% ESBA903 in hexPLA of 2500 g/mol and 5000 g/mol. 50 mg were filled into Eppendorf cups and stored at 4° C. and 37° C., respectively under light protection. After 4 weeks and 10 weeks, the protein was extracted from 10 mg of the sample formulations by vortexing with citrate buffer, as described above. The supernatant was analyzed by SEC-HPLC regarding the percentage of the ESBA903 monomer peak area relative to the total peak area.

Stability over long time periods is an issue for protein formulations. They are generally stored under refrigerated conditions to prevent denaturation even as lyophilisates. Therefore, a stability study of ESBA903-hexPLA formulations was performed. Samples containing 5.0% ESBA903 in hexPLA of 2500 g/mol and 5000 g/mol were stored at 4° C. After 4 and 10 weeks the protein was extracted from the polymer and analyzed by SEC-HPLC.

Table 2 summarizes the relative peak areas of the ESBA903 monomer compared to the peak area of the total extracted protein. Both formulations showed similar results under equal storage conditions, independent of the hexPLA molecular weight. Since the molecular weight determined the number of present polymer chains and thus of the polymer end groups, a considerable influence of the hydroxy- and carboxy-moieties on the protein was minimal, if not excludable. At 4° C. the rate of the protein monomer remained above 97% during the entire study period, proving that ESBA903 was not only compatible with hexPLA but also stable inside the polymer. Thus, the application-ready ESBA903-hexPLA formulations could be stored under standard refrigerator conditions as defined by the ICH. Since the monomer values remained above 97% without exhibiting a negative trend, storage times exceeding 10 weeks seem feasible as would be needed for convenient handling.

TABLE 2

| Formulation containing 5.00% | Storage temperature | Relative area ESBA903 monomer [%] | | |
|---|---|---|---|---|
| ESBA903 in: | [° C.] | 0 weeks | 4 weeks | 10 weeks |
| hexPLA 2500 g/mol | 4 | 97.4 | 98.4 | 97.5 |
| | 37 | 97.4 | 94.8 | 94.5 |
| hexPLA 5000 g/mol | 4 | 97.7 | 98.0 | 98.3 |
| | 37 | 97.7 | 96.0 | 92.5 |

Example 5

Protective Effect of hexPLA on ESBA903

To investigate the stability of ESBA903 at body temperature, formulations were stored at 37° C. and analyzed after 4 and 10 weeks by SEC-HPLC (Table 2).

Both formulations with hexPLA of 2500 g/mol and 5000 g/mol, respectively displayed a slight trend of decreasing monomer, while dimers and multimers of ESBA903 were formed in the matrix. Nevertheless, the monomeric fraction remained above 90% after 10 weeks, suggesting that ESBA903-hexPLA suspensions were rather stable at 37° C., and that apparently no significant alterations in protein conformation took place. Most interestingly, with over 90% active monomer content, the protein was more stable in lyophilized state in the hexPLA polymer matrix at this temperature than in the buffer solution, from which only 71% of active protein were recovered after 10 weeks. The lyophilized protein was protected by the hydrophobic matrix, which prevented contact with the aqueous environment until its release.

Example 6

ESBA903 Formulation Stability in Buffer Solution for In Vitro Release

Samples in citrate buffer solution containing 0.12 mg/mL ESBA903 were stored at 37° C. for 10 weeks. In a second approach under the same storage conditions, 2.2 mg/mL 2-hydroxyoctanoic acid were added as the final degradation product to investigate the influence of the degrading polymer on the protein stability. All experiments were done in duplicates. The amounts of the ESBA903 monomer were determined by SE-HPLC after 2 and 10 weeks.

A prescreening of different buffer systems revealed the citrate buffer with a pH of 6.5 as the best choice for this antibody fragment. In this work, the stability in this buffer solution was evaluated by SEC-HPLC, quantifying the ESBA903 monomer concentration, in the presence and absence of 2-hydroxyoctanoic acid as the final degradation product of hexPLA. In the pure buffer solution under release conditions, the ESBA903 monomer concentration decreased to 84% of its initial value after 10 weeks due to aggregation. In the buffer solution with added polymer degradation product, the monomer content was slightly lower with 71% after 10 weeks, assumingly related to the decrease in the pH-value. For the intended feasibility study of the sustained-release characteristics, the monomer stability above 70% was rated sufficient for a release test covering several weeks. However, the time dependent decreasing amount of monomer antibody fragments resulted in an underestimation of the released ESBA903 concentration in in vitro release experiments, especially for later time points.

After placing the ESBA903-hexPLA formulations into the aqueous buffer solution, the formulations formed single droplets of spherical shape (FIG. 4), due to the high hydrophobicity of the polymer and its tendency to minimize its surface in the hydrophilic environment. All formulations with polymer molecular weights of 1500 g/mol to 3500 g/mol maintained the spherical shape throughout the investigated three months. Only the most viscous formulations in hexPLA of 5000 g/mol disintegrated rather fast during the first 72 hour resulting in small formulation droplets. This was presumably due to a solvent drag into the formulation caused by the lyophilized protein preparation, whereby the continuous inflow of water formed channels stretching the formulation droplet until it diverged. In contrast, the less viscous formulations with lower molecular weight hexPLAs were more flexible, what might compensate an initial solvent drag, and thus maintained the shape.

Example 7

ESBA903 In Vitro Release

To verify first the suitability of the release system, the behavior of the formulation and the protein in the aqueous release environment were tested. Afterwards, an in vitro study covering the influence on the release characteristics of the drug loading, the polymer molecular weight, and the amount of applied formulation was performed to identify good formulation candidates for ophthalmic sustained-release applications.

50±0.5 mg of the formulations were weighed into 20 mL sealable glass vials. The formulation containing 5.0% drug in hexPLA of 2500 g/mol was additionally investigated with 25±0.5 mg of formulation. 20 mL of citrate buffer (50 mM sodium citrate, 72 mM NaCl, 8 mM $NaN_3$, pH-value 6.25) as the release medium were added. The samples were incubated at 37° C. and shaking at 60 rpm. 1 mL of the release-solution was taken from each vial after 1 and 3 days, after 1, 2, 3 and 4 weeks, followed by sampling every second week until week 14. Each time, the same volume of fresh citrate buffer was refilled to maintain the buffer volume constant. The ESBA903 concentration in the release samples was determined by SEC-HPLC.

Figure 5A:
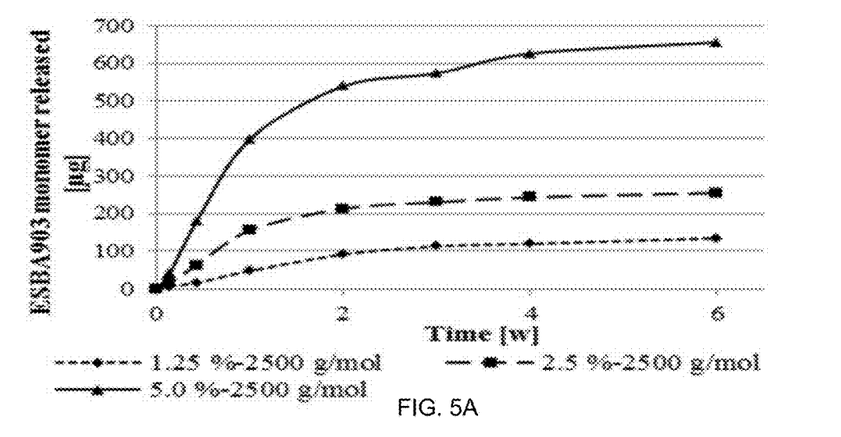
FIG. 5A shows cumulative release of ESBA903 from formulations with drug loadings between 1.25% and 5.0% and a hexPLA molecular weight of 2500 g/mol.
Figure 5B:
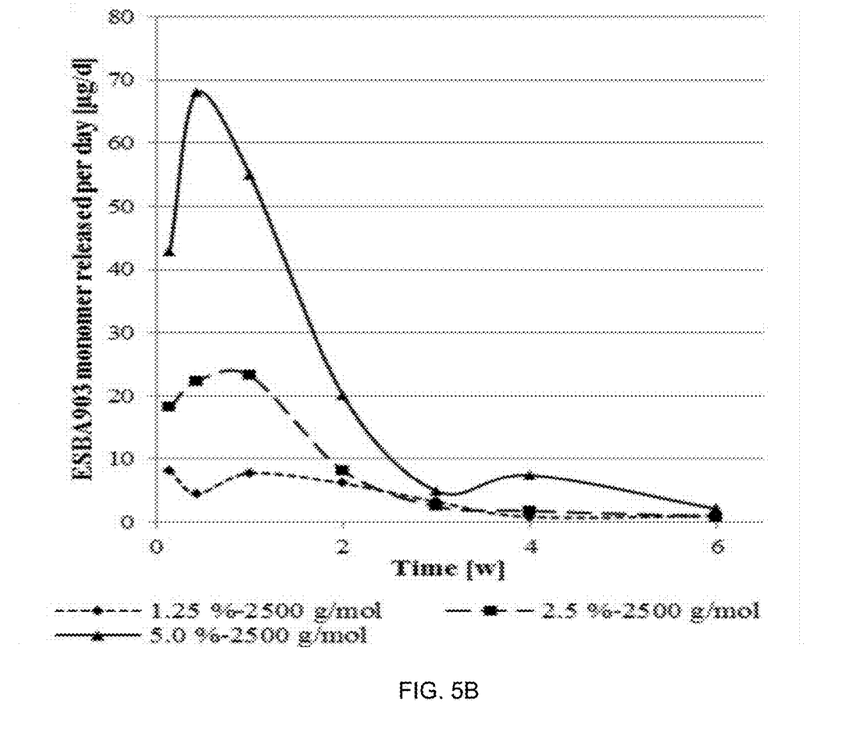
FIG. 5B shows release of ESBA903 monomer per day from formulations with drug loadings between 1.25% and 5.0% and a hexPLA molecular weight of 2500 g/mol.

To investigate the influence of the formulation drug loading on the release behavior, three formulations were prepared using the same hexPLA polymer of 2500 g/mol and ESBA903 loadings of 1.25%, 2.5%, and 5.0%. FIG. 5 shows the cumulative in vitro release of ESBA903 monomer and the daily release of these formulations over 6 weeks analyzed by SEC-HPLC. All three formulations displayed a similar release profile, differing only in the amount of released monomer of the single chain antibody fragment. During the first 2 to 3 weeks, the ESBA903 monomer was faster released from the polymer matrix, and subsequently, the release was constant at lower rates until week 6.

Viewing the release curves in more detail, the fast release in the first 3 weeks can be explained by the release of protein molecules close to the surface of the depot. Most interestingly, no pronounced burst release was observed for the ESBA903-hexPLA formulations as it is known for many sustained-release formulations, e.g. with poly(lactic acid) (Maincent et al., 2009, *European Journal of Pharmaceutics and Biopharmaceutics* 73:337). Presumably, the liquid hexPLA polymer entirely covered the incorporated lyophilized protein preparation, shielding it from immediate dissolution. After 3 weeks the release rate decreased, presumably because the active compound was less accessible by the aqueous solution.

A difference in the relative release rate between the three drug loading formulations was only detectable during the first 2 to 3 weeks. With higher drug loadings the protein monomer release increased in the range between 1.25% and 5.0%. Since less of the polymer needs to be degraded in the beginning and the dissolution of the lyophilized drug preparation facilitates additional infiltration of water, the formulation with 5.0% ESBA903 released fastest in the initial phase.

In these classical in vitro tests a sustained-release was detectable for 6 weeks for the ESBA903-hexPLA formulations. This long duration is a significant improvement compared to the immediate release formulations currently marketed.

Figure 6A:
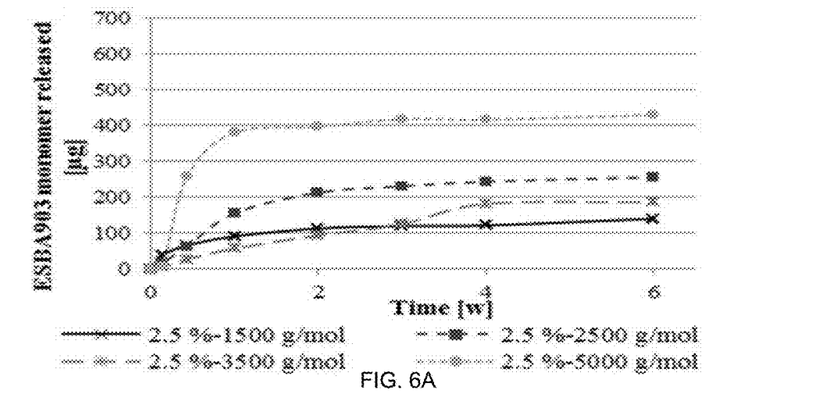
FIG. 6A shows cumulative release of ESBA903 from formulations with 2.5% drug loading and different hexPLA molecular weights between 1500 g/mol and 5000 g/mol.
Figure 6B:
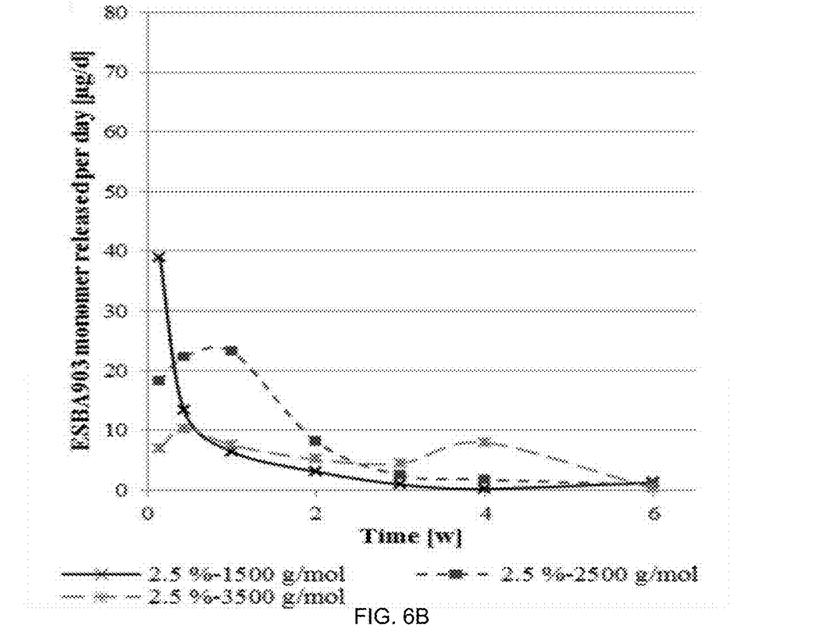
FIG. 6B shows release of ESBA903 monomer per day from formulations with 2.5% drug loading and different hexPLA molecular weights between 1500 g/mol and 5000 g/mol.

FIG. 6 summarizes the release data of the antibody monomer of a 6 weeks study for four formulations with the same drug loading of 2.5% but with different hexPLA molecular weights of 1500 g/mol, 2500 g/mol, 3500 g/mol, and 5000 g/mol. The release profile of the formulation with hexPLA of 5000 g/mol differed with its pronounced release considerably from the formulations with the smaller molecular weights. A slower release could be expected for formulations with higher molecular weights since more ester bonds would need to be hydrolysed before the polymer was degraded and the drug released. However, the disintegration of the spherical depot of the 5000 g/mol formulation in the buffer solution as described before, lead to a significant increase in the formulation surface resulting in a faster release.

The 3500 g/mol and 2500 g/mol suspensions liberated the protein as expected, showing slower release for the formulation with the higher molecular weight. Furthermore, the period of pronounced release was longer for the formulation with 3500 g/mol reaching 4 weeks. In the later stage at 6 weeks both formulations resulted in a similar rate of release.

The ESBA903-hexPLA formulation with the polymer of 1500 g/mol showed a faster release compared to the 2500 g/mol and 3500 g/mol polymer during the first day, but then the daily release slowed down faster. The higher concentrations in the beginning were due to the lower viscosity and faster dissolution of accessible water soluble hexPLA oligomers, what might lead to an easier intrusion of water and release of active compound. Then presumably, a layer of protein free polymer formed out on the surface of the depot, rapidly decreasing the release rate. Nevertheless, also this formulation showed a release period of at least 6 weeks.

Figure 7A:
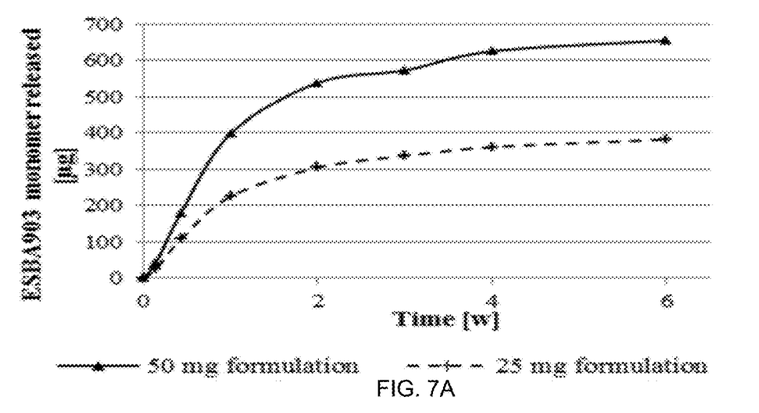
FIG. 7A shows cumulative release of ESBA903 from 50 mg and 25 mg of formulation containing 2.5% ESBA903 in hexPLA of 2500 g/mol.
Figure 7B:
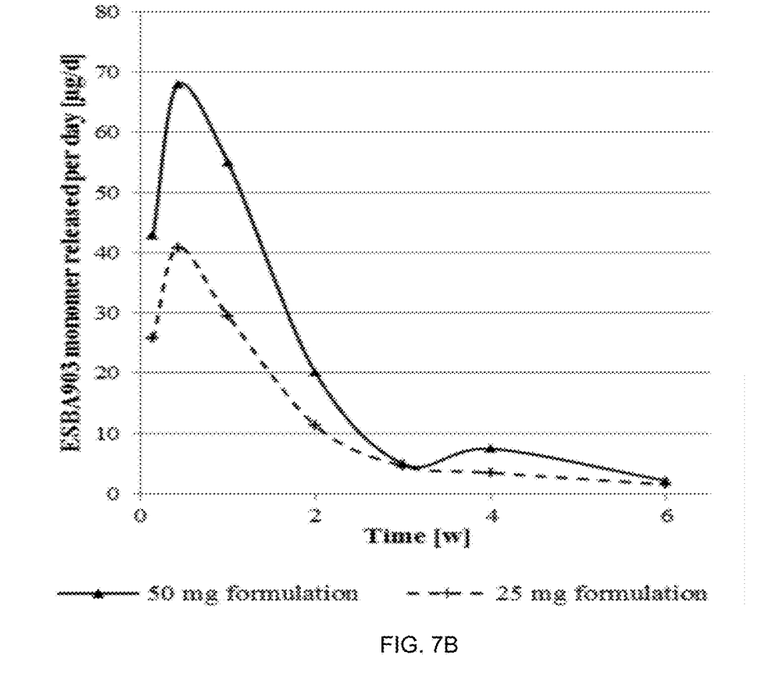
FIG. 7B shows release of ESBA903 monomer per day from 50 mg and 25 mg of formulation containing 2.5% ESBA903 in hexPLA of 2500 g/mol.

In FIG. 7 the release profiles of two samples containing 2.5% ESBA903 in the hexPLA polymer of 2500 g/mol are displayed, which differed in the mass of the formulation droplet. Both samples showed a similar release profile over the entire 6 weeks, showing that the release characteristics were unaffected by the formulation amount.

Investigation of the ESBA903 Release Exceeding 6 Weeks

Figure 8:
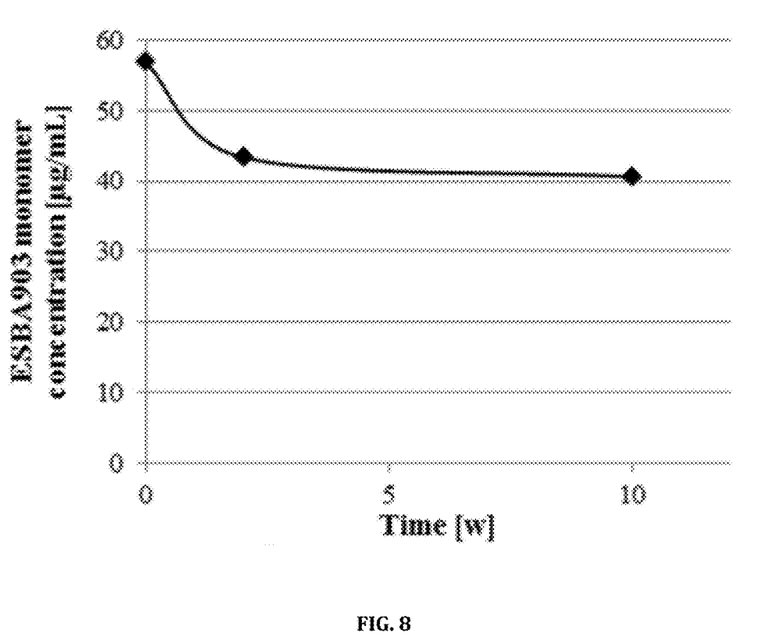
FIG. 8 shows concentration decrease of ESBA903 monomer in citrate buffer in the presence of 2-hydroxyoctanoic acid stored at 37° C.
Figure 9:
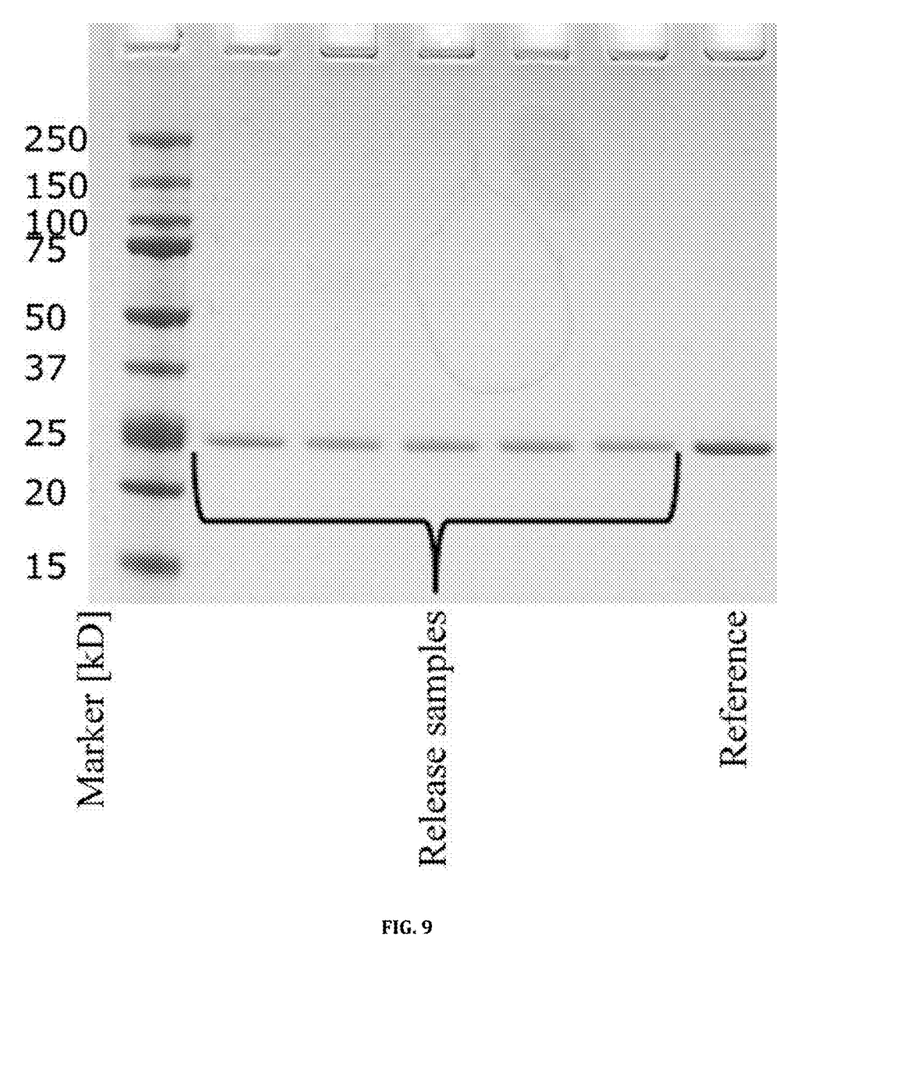

A general problem for the in vitro sustained-release tests of proteins is their limited stability in aqueous buffer solution, potentially resulting in degradation, oligomerization and precipitation of the released active substance. For ESBA903, the decline in the monomer concentration in the citrate buffer during 10 weeks is shown in FIG. 8. Over time more and more of the released protein degrades in solution, counteracting the new release from the matrix, which results an underestimation of the real protein release. Thus, the studied release period from 6 to 14 weeks is here discussed separately from the first 6 weeks due to the decreasing ESBA903 concentrations with time Table 3 summarizes the ESBA903 monomer concentrations in the release medium of the seven release samples between week 6 and 14. All samples showed almost constant concentrations, despite the known limited stability of the protein monomer in the buffer solution after release. The constant monomer concentrations can be explained by the fact that the protein monomer aggregation in the buffer solution comes to equilibrium with its further release from the polymer matrix. Thus, the overall release period of these formulations is probably much longer than 6 and 8 weeks, respectively.

TABLE 3

| Formulation amount [mg] | Sample composition Amount of ESBA903 in hexPLA of certain molecular weight | ESBA903 monomer concentration in release medium [μg/mL] | | | | |
|---|---|---|---|---|---|---|
| | | 6 w | 8 w | 10 w | 12 w | 14 w |
| 50 | 1.25%-2500 g/mol | 9.0 | 8.4 | 7.7 | 7.4 | 7.3 |
| 50 | 2.50%-2500 g/mol | 17.0 | 17.4 | 16.2 | 15.2 | 14.7 |
| 50 | 5.00%-2500 g/mol | 43.7 | 44.0 | 41.7 | 39.8 | 37.2 |
| 50 | 2.50%-1500 g/mol | 9.3 | 9.2 | 8.5 | 8.6 | 8.4 |
| 50 | 2.50%-3500 g/mol | 12.4 | 12.4 | 12.0 | 11.6 | 10.8 |
| 50 | 2.50%-5000 g/mol | 28.5 | 28.8 | 26.8 | 26.6 | 26.1 |
| 25 | 5.00%-2500 g/mol | 25.4 | 25.7 | 25.7 | 27.3 | 27.9 |

The sample with 25 mg of the formulation containing 5.0% ESBA903 in hexPLA of 2500 g/mol released the protein continuously over the whole period of 14 weeks, showing steadily increasing ESBA903 monomer concentrations. The more pronounced release from the 25 mg of formulation was probably due to the higher surface to volume ratio, facilitating polymer degradation and resulting in a predominance of protein release. Nevertheless, small amounts of ESBA903-hexPLA formulation may be advantageous regarding ease of application and their release profile.

Example 8

Protein Integrity and Activity after In Vitro Release

Next to the sustained-release profiles, the stability and the activity of the released single chain antibody fragment were assessed to evaluate the quality of the released protein. Therefore, samples from the release experiments were analyzed using sodium dodecyl sulfate polyacrylamide gel electrophoresis (SDS-PAGE) to control the integrity of the released protein monomer, and surface plasmon resonance analysis to investigate its activity. The in vitro release samples of the final time point at week 14 were compared to a freshly prepared ESBA903 reference. Protein species were separated on a NuPAGE Novex 12% Bis-Tris gel (Life Technologies Corporation, Grand Island, USA) using the buffers and reagents provided by the manufacturer. The protein bands were then stained using Coomassie Blue.

The resulting SDS-PAGE gel is displayed in FIG. 9. Both, the reference and the release samples showed only one band at 25 kDa at the calculated molecular weight of the antibody fragment. This affirmed the data obtained before by SEC and indicated that the chemical structure of the released antibody fragment was maintained during incorporation in the hexPLA matrix and release into the buffer.

The affinity of the released ESBA903 monomer toward human VEGF was measured using surface plasmon resonance analysis in comparison to a fresh ESBA903 reference. For evaluation of the binding kinetics, surface plasmon resonance measurements using a BIAcore T100 were performed. Carboxymethylated dextran biosensor chips (CM4, GE HealthCare, Uppsala, Sweden) were activated with N-ethyl-N'-(3-dimethylaminopropyl) carbodiimide hydrochloride and N-hydroxysuccinimide according to the supplier's instructions. Recombinant human $VEGF_{165}$ (Pep roTech EC Ltd., London, UK) was immobilized on a CM4 sensor chip using a standard amine-coupling procedure to achieve a response of approximately 500 resonance units. 2-fold serial dilutions (2.5-20 nM) of ESBA903 standard and formulation samples in HBS-EP buffer (10 mM HEPES, 150 mM NaCl, 3 mM EDTA, and 0.05% surfactant P20, pH 7.4) were injected into the flow cells at a flow rate of 30 μL/min for 5 minutes. Dissociation of the anti-VEGF scFv from the VEGF on the CM4 chip was allowed to proceed for 10 minutes. After each injection cycle, surfaces were regenerated with 2 injections of 100 mM NaOH.

The apparent dissociation ($k_d$) and association ($k_a$) rate constants and the apparent dissociation equilibrium constant ($K_D$) were calculated with BIAcore T100 evaluation Software version 2.0.1 using a one-to-one Langmuir binding model (Biacore Inc., Uppsala, Sweden).

Three formulations were analyzed, including the formulations with 2.5% and 5.0% ESBA903 in hexPLA of 2500 g/mol and 2.5% in the 3500 g/mol polymer. Table 4 summarizes the obtained affinity data for the investigated time points after 3 days, 4, and the final 14 weeks.

TABLE 4

| Sample - Amount of ESBA903 in hexPLA of certain molecular weight | Time | ka [1/Ms] | kd [1/s] | KD [M] |
|---|---|---|---|---|
| 100% ESBA903 in buffer | 0 | $9.56 \times 10^5$ | $2.45 \times 10^{-5}$ | $2.56 \times 10^{-11}$ |
| 2.5%-2500 g/mol | 3 d | $5.29 \times 10^5$ | $2.59 \times 10^{-5}$ | $4.89 \times 10^{-11}$ |
| | 4 w | $4.24 \times 10^5$ | $2.34 \times 10^{-5}$ | $5.52 \times 10^{-11}$ |
| | 14 w | $4.07 \times 10^5$ | $3.11 \times 10^{-5}$ | $7.62 \times 10^{-11}$ |
| 5.0%-2500 g/mol | 3 d | $4.65 \times 10^5$ | $2.77 \times 10^{-5}$ | $5.94 \times 10^{-11}$ |
| | 4 w | $5.54 \times 10^5$ | $3.56 \times 10^{-5}$ | $6.43 \times 10^{-11}$ |
| | 14 w | $4.21 \times 10^5$ | $2.78 \times 10^{-5}$ | $6.60 \times 10^{-11}$ |
| 2.5%-3500 g/mol | 3 d | $4.39 \times 10^5$ | $3.00 \times 10^{-5}$ | $6.85 \times 10^{-11}$ |
| | 4 w | $5.82 \times 10^5$ | $3.03 \times 10^{-5}$ | $5.21 \times 10^{-11}$ |
| | 14 w | $4.08 \times 10^5$ | $3.37 \times 10^{-5}$ | $8.26 \times 10^{-11}$ |

The samples of three formulations at 3 days, 4, and 14 weeks are compared to an ESBA903 reference (ka = association rate constant; kd = dissociation rate constant; KD = equilibrium dissociation constant)

All samples, independent of the formulation and time point, showed similar results for the association and dissociation rate constant and thus also for the equilibrium dissociation constant. The release samples showed comparable constants to the scFv reference.

Together with the low dissociation constant, the high association constants of more than $10^5$ $M^{-1}$ $s^{-1}$ reflect the high affinity of the antibody fragment monomer to human VEGF, emphasizing its potency to scavenge the growth factor molecule. The slightly lower association constants of the samples compared to the reference were most probably due to imprecision in the protein monomer quantification. This assumption was supported by the fact of similar dissociation rate constants between samples and reference, which are independent of the concentration. The measured dissociation rate constants resulted in low equilibrium dissociation constants for the release samples at all time points up to 14 weeks. Thus, the antibody fragment monomers released from the hexPLA matrix were in their biologically active form over the whole sustained-release period of more than 3 months. Neither the drug loading nor the polymer molecular weight had a significant influence on the equilibrium dissociation constant, therefore they do not affect the protein structure, which otherwise would have resulted in an activity decrease. This further proved that hexPLA showed in vitro suitability as a parenteral sustained-release excipient for ESBA903, because it preserved and released the pharmaceutically active monomer of the antibody fragment.

It should be understood that the foregoing disclosure emphasizes certain specific embodiments of the invention and that all modifications or alternatives equivalent thereto are within the spirit and scope of the invention as set forth in the appended claims.

What is claimed is:

1. A process for the preparation of a sustained-release pharmaceutical formulation, the process comprising cryo-milling a single chain antibody and hexylsubstituted poly (lactic acid) (hexPLA), wherein the single chain antibody comprises the amino acid sequence of SEQ ID NO: 1, and wherein the single chain antibody is present in a final concentration in the range of 1.25% to 5.0% (w/w) and the hexPLA is present at a molecular weight in the range of 2500 g/mol to 5000 g/mol.

* * * * *

SEQUENCE LISTING

<160> NUMBER OF SEQ ID NOS: 1

<210> SEQ ID NO 1
<211> LENGTH: 251
<212> TYPE: PRT
<213> ORGANISM: Artificial Sequence
<220> FEATURE:
<223> OTHER INFORMATION: synthetic peptide scFv

<400> SEQUENCE: 1

```
Glu Ile Val Met Thr Gln Ser Pro Ser Thr Leu Ser Ala Ser Val Gly
1               5                   10                  15

Asp Arg Val Ile Ile Thr Cys Gln Ala Ser Glu Ile Ile His Ser Trp
            20                  25                  30

Leu Ala Trp Tyr Gln Gln Lys Pro Gly Lys Ala Pro Lys Leu Leu Ile
        35                  40                  45

Tyr Leu Ala Ser Thr Leu Ala Ser Gly Val Pro Ser Arg Phe Ser Gly
50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Asn Val Tyr Leu Ala Ser Thr
                85                  90                  95

Asn Gly Ala Asn Phe Gly Gln Gly Thr Lys Leu Thr Val Leu Gly Gly
            100                 105                 110

Gly Gly Gly Ser Gly Gly Gly Gly Ser Gly Gly Gly Ser Gly Gly
            115                 120                 125

Gly Gly Ser Glu Val Gln Leu Val Glu Ser Gly Gly Gly Leu Val Gln
    130                 135                 140

Pro Gly Gly Ser Leu Arg Leu Ser Cys Thr Ala Ser Gly Phe Ser Leu
145                 150                 155                 160

Thr Asp Tyr Tyr Tyr Met Thr Trp Val Arg Gln Ala Pro Gly Lys Gly
                165                 170                 175

Leu Glu Trp Val Gly Phe Ile Asp Pro Asp Asp Pro Tyr Tyr Ala
            180                 185                 190

Thr Trp Ala Lys Gly Arg Phe Thr Ile Ser Arg Asp Thr Ser Lys Asn
        195                 200                 205

Thr Val Tyr Leu Gln Met Asn Ser Leu Arg Ala Glu Asp Thr Ala Val
    210                 215                 220

Tyr Tyr Cys Ala Gly Gly Asp His Asn Ser Gly Trp Gly Leu Asp Ile
225                 230                 235                 240

Trp Gly Gln Gly Thr Leu Val Thr Val Ser Ser
                245                 250
```